United States Patent
Lively et al.

(10) Patent No.: US 8,314,315 B1
(45) Date of Patent: Nov. 20, 2012

(54) WHEAT VARIETY 25W36

(75) Inventors: Kyle J. Lively, Tipton, IN (US);
Gregory C. Marshall, Arcadia, IN (US);
William J. Laskar, Tipton, IN (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 281 days.

(21) Appl. No.: 12/758,269

(22) Filed: Apr. 12, 2010

Related U.S. Application Data

(63) Continuation of application No. 12/099,240, filed on Apr. 8, 2008, now abandoned.

(51) Int. Cl.
*A01H 1/00* (2006.01)
*A01H 5/00* (2006.01)
*A01H 5/10* (2006.01)
*A01H 4/00* (2006.01)
*C12N 15/82* (2006.01)

(52) U.S. Cl. ............ 800/320.3; 800/260; 800/264; 800/278; 800/279; 800/284; 800/300; 800/301; 800/302; 800/303; 435/410

(58) Field of Classification Search .................. None
See application file for complete search history.

(56) References Cited

OTHER PUBLICATIONS

Plant Variety Protect Act, Certificate No. 9200159 for Wheat "2737W", issued Apr. 30, 1993.*
Plant Variety Protection Act, Certificate No. 9200159 for Wheat '2737W' issued Apr. 30, 1993.
Plant Variety Protection Act, Certificate No. 200700368 for Wheat, Common '25W36' issued Sep. 17, 2007.

* cited by examiner

*Primary Examiner* — Cynthia Collins
(74) *Attorney, Agent, or Firm* — Alston & Bird LLP

(57) ABSTRACT

A wheat variety designated 25W36, the plants and seeds of wheat variety 25W36, methods for producing a wheat plant produced by crossing the variety 25W36 with another wheat plant, and hybrid wheat seeds and plants produced by crossing the variety 25W36 with another wheat line or plant, and the creation of variants by mutagenesis or transformation of variety 25W36. This invention also relates to methods for producing other wheat varieties or breeding lines derived from wheat variety 25W36 and to wheat varieties or breeding lines produced by those methods.

34 Claims, No Drawings

WHEAT VARIETY 25W36

CROSS-REFERENCE TO RELATED APPLICATION

This application is a continuation of U.S. application Ser. No. 12/099,240, filed Apr. 8, 2008 now abandoned, which is herein incorporated by reference.

FIELD OF INVENTION

This invention is in the field of wheat (*Triticum aestivum* L.) breeding, specifically relating to a wheat variety designated 25W36.

BACKGROUND OF INVENTION

Wheat is grown worldwide and is the most widely adapted cereal. There are five main wheat market classes. They include the four common wheat (*Triticum aestivum* L.) classes: hard red winter, hard red spring, soft red winter, and white. The fifth class is durum (*Triticum turgidum* L.). Common wheats are used in a variety of food products such as bread, cookies, cakes, crackers, and noodles. In general the hard wheat classes are milled into flour used for breads and the soft wheat classes are milled into flour used for pastries and crackers. Wheat starch is used in the food and paper industries, as laundry starches, and in other products. Because of its use in baking, the grain quality of wheat is very important. To test the grain quality of wheat for use as flour, milling properties are analyzed. Important milling properties are relative hardness or softness, weight per bushel of wheat (test weight), siftability of the flour, break flour yield, middlings flour yield, total flour yield, flour ash content, and wheat-to-flour protein conversion. Good processing quality for flour is also important. Good quality characteristics for flour from soft wheats include low to medium-low protein content, a low water absorption, production of large-diameter test cookies and large volume cakes. Wheat glutenins and gliadins, which together confer the properties of elasticity and extensibility, play an important role in the grain quality. Changes in quality and quantity of these proteins change the end product for which the wheat can be used.

The present invention relates to a new and distinctive wheat variety, designated 25W36 which has been the result of years of careful breeding and selection as part of a wheat breeding program. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, tolerance to drought and heat, improved grain quality, and better agronomic qualities.

Field crops are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The term cross-pollination herein does not include self-pollination or sib-pollination. Wheat plants (*Triticum aestivum* L.), are recognized to be naturally self-pollinated plants which, while capable of undergoing cross-pollination, rarely do so in nature. Thus intervention for control of pollination is critical to the establishment of superior varieties.

A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny. The term "homozygous plant" is hereby defined as a plant with homozygous genes at 95% or more of its loci. The term "inbred" as used herein refers to a homozygous plant or a collection of homozygous plants.

Choice of breeding or selection methods depends on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. In general breeding starts with the crossing of two genotypes (a "breeding cross"), each of which may have one or more desirable characteristics that is lacking in the other or which complements the other. If the two original parents do not provide all the desired characteristics, other sources can be included by making more crosses. In each successive filial generation, F1→F2; F2→F3; F3→F4; F4→F5, etc., plants are selfed to increase the homozygosity of the line. Typically in a breeding program five or more generations of selection and selfing are practiced to obtain a homozygous plant.

Pedigree breeding is commonly used for the improvement of self-pollinating crops. Two parents that possess favorable, complementary traits are crossed to produce an F1. An F2 population is produced by selfing or sibbing one or several F1's. Selection of the best individuals may begin in the F2 population; then, beginning in the F3, the best individuals in the best families are selected. Replicated testing of families can begin in the F4 generation to improve the effectiveness of selection for traits with low heritability. At an advanced stage of inbreeding (i.e., F5, F6 and F7), the best lines or mixtures of phenotypically similar lines are tested for potential release as new varieties.

Backcross breeding has been used to transfer genes for simply inherited, qualitative, traits from a donor parent into a desirable homozygous variety that is utilized as the recurrent parent. The source of the traits to be transferred is called the donor parent. After the initial cross, individuals possessing the desired trait or traits of the donor parent are selected and then repeatedly crossed (backcrossed) to the recurrent parent. The resulting plant is expected to have the attributes of the recurrent parent (e.g., variety) plus the desirable trait or traits transferred from the donor parent. This approach has been used extensively for breeding disease resistant varieties.

Each wheat breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination and the number of hybrid offspring from each successful cross. Recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Plants from the populations can be selected and selfed to create new varieties.

Another breeding method is single-seed descent. This procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed. In a multiple-seed procedure, wheat breeders commonly harvest one or more spikes (heads) from each plant in a population and thresh them together to form a bulk. Part of the bulk is used to plant the next generation and part is put in reserve. The procedure has been referred to as modified single-seed descent. The multiple-seed procedure has been used to save labor at harvest. It is considerably faster to thresh spikes with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Bulk breeding can also be used. In the bulk breeding method an F2 population is grown. The seed from the populations is harvested in bulk and a sample of the seed is used to make a planting the next season. This cycle can be repeated several times. In general when individual plants are expected to have a high degree of homozygosity, individual plants are selected, tested, and increased for possible use as a variety.

Molecular markers including techniques such as Starch Gel Electrophoresis, Isozyme Eletrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs) may be used in plant breeding methods. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program (Openshaw et al. Marker-assisted Selection in Backcross Breeding. In: Proceedings Symposium of the Analysis of Molecular Marker Data, 5-6 Aug. 1994, pp. 41-43. Crop Science Society of America, Corvallis, Oreg.). The use of molecular markers in the selection process is often called Genetic Marker Enhanced Selection.

The production of double haploids can also be used for the development of homozygous lines in the breeding program. Double haploids are produced by the doubling of a set of chromosomes (1N) from a heterozygous plant to produce a completely homozygous individual. This can be advantageous because the process omits the generations of selfing needed to obtain a homogygous plant from a heterozygous source. Various methodologies of making double haploid plants in wheat have been developed (Laurie, D. A. and S. Reymondie, *Plant Breeding*, 1991, v. 106:182-189. Singh, N. et al., *Cereal Research Communications*, 2001, v. 29:289-296; Redha, A. et al., *Plant Cell Tissue and Organ Culture*, 2000, v. 63:167-172; U.S. Pat. No. 6,362,393)

Though pure-line varieties are the predominate form of wheat grown for commercial wheat production hybrid wheat is also used. Hybrid wheats are produced with the help of cytoplasmic male sterility, nuclear genetic male sterility, or chemicals. Various combinations of these three male sterility systems have been used in the production of hybrid wheat.

Descriptions of other breeding methods that are commonly used for different traits and crops can be found in one of several reference books (e.g., Allard, *Principles of Plant Breeding*, 1960; Simmonds, *Principles of Crop Improvement*, 1979; editor Heyne, *Wheat and Wheat Improvement*, 1987; Allan, "Wheat", Chapter 18, *Principles of Crop Development*, vol. 2, Fehr editor, 1987).

Promising advanced breeding lines are thoroughly tested and compared to appropriate standards in environments representative of the commercial target area(s). The best lines are candidates for new commercial varieties; those still deficient in a few traits may be used as parents to produce new populations for further selection.

A most difficult task is the identification of individuals that are genetically superior, because for most traits the true genotypic value is masked by other confounding plant traits or environmental factors. One method of identifying a superior genotype is to observe its performance relative to other experimental genotypes and to a widely grown standard variety. Generally a single observation is inconclusive, so replicated observations are required to provide a better estimate of its genetic worth.

A breeder uses various methods to help determine which plants should be selected from the segregating populations and ultimately which lines will be used for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which lines are significantly better or different for one or more traits of interest. Experimental design methods are used to control error so that differences between two lines can be more accurately determined. Statistical analysis includes the calculation of mean values, determination of the statistical significance of the sources of variation, and the calculation of the appropriate variance components. Five and one percent significance levels are customarily used to determine whether a difference that occurs for a given trait is real or due to the environment or experimental error.

Plant breeding is the genetic manipulation of plants. The goal of wheat breeding is to develop new, unique and superior wheat varieties. In practical application of a wheat breeding program, the breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop exactly the same line.

Each year, the plant breeder selects the germplasm to advance to the next generation. This germplasm is grown under unique and different geographical, climatic and soil conditions, and further selections are then made during and at the end of the growing season.

Proper testing should detect major faults and establish the level of superiority or improvement over current varieties. In addition to showing superior performance, there must be a demand for a new variety. The new variety must be compatible with industry standards, or must create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. It must also be feasible to produce seed easily and economically.

These processes, which lead to the final step of marketing and distribution, can take from six to twelve years from the time the first cross is made. Therefore, development of new varieties is a time-consuming process that requires precise forward planning, efficient use of resources, and a minimum of changes in direction.

Wheat (*Triticum aestivum* L.), is an important and valuable field crop. Thus, a continuing goal of wheat breeders is to develop stable, high yielding wheat varieties that are agronomically sound and have good grain quality for its intended use. To accomplish this goal, the wheat breeder must select and develop wheat plants that have the traits that result in superior varieties.

SUMMARY OF INVENTION

According to the invention, there is provided a novel wheat variety, designated 25W36. This invention thus relates to the seeds of wheat variety 25W36, to the plants of wheat variety 25W36 and to methods for producing a wheat plant produced by crossing wheat variety 25W36 with another wheat plant, and the creation of variants by mutagenesis or transformation of wheat 25W36. This invention relates to transgenic backcross conversions of wheat variety 25W36. This invention also relates to methods for developing other wheat varieties or breeding lines derived from wheat variety 25W36 and to wheat varieties or breeding lines produced by those methods. Wheat variety 25W36 demonstrates a unique combination of traits including outstanding yield potential, excellent winter hardiness, excellent stripe rust resistance, very good resistance to leaf rust, powdery mildew and spindle streak mosaic virus and very good test weight.

DETAILED DESCRIPTION OF INVENTION

A wheat variety needs to be highly homogeneous, homozygous and reproducible to be useful as a commercial variety. There are many analytical methods available to determine the homozygotic stability, phenotypic stability, and identity of these varieties.

The oldest and most traditional method of analysis is the observation of phenotypic traits. The data is usually collected in field experiments over the life of the wheat plants to be examined. Phenotypic characteristics most often observed are for traits such as seed yield, head configuration, glume configuration, seed configuration, lodging resistance, disease resistance, maturity, etc.

In addition to phenotypic observations, the genotype of a plant can also be examined. There are many laboratory-based techniques available for the analysis, comparison and characterization of plant genotype; among these are Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). Gel electrophoresis is particularly useful in wheat. Wheat variety identification is possible through electrophoresis of gliadin, glutenin, albumin and globulin, and total protein extracts (Bietz, J. A., pp. 216-228, "Genetic and Biochemical Studies of Nonenzymatic Endosperm Proteins" In *Wheat and Wheat Improvement*, ed. E. G. Heyne, 1987).

The variety of the invention has shown uniformity and stability for all traits, as described in the following variety description information. It has been self-pollinated a sufficient number of generations, with careful attention to uniformity of plant type to ensure homozygosity and phenotypic stability. The line has been increased with continued observation for uniformity. No variant traits have been observed or are expected in 25W36, as described in Table 1 (Variety Description Information).

Wheat variety 25W36 is a common, soft white winter wheat. Variety 25W36 demonstrates outstanding yield potential, excellent winter hardiness, excellent stripe rust resistance, very good resistance to leaf rust, powdery mildew and spindle streak mosaic virus and very good test weight.

Variety 25W36 is particularly adapted to the Northern soft wheat region of the United States.

Wheat variety 25W36, being substantially homozygous, can be reproduced by planting seeds of the line, growing the resulting wheat plants under self-pollinating or sib-pollinating conditions, and harvesting the resulting seed, using techniques familiar to the agricultural arts.

Definitions for Area of Adaptability

When referring to area of adaptability, such term is used to describe the location with the environmental conditions that would be well suited for this wheat variety. Area of adaptability is based on a number of factors, for example: days to heading, winter hardiness, insect resistance, disease resistance, and drought resistance. Area of adaptability does not indicate that the wheat variety will grow in every location within the area of adaptability or that it will not grow outside the area.

Northern area=States of DE, IL, IN, MI, MO, NJ, NY, OH, PA, WI and Ontario, Canada Mid-south=States of AR, KY, MO bootheel and TN Southeast=States of NC, SC, and VA Deep South=States of AL, GA, LA, and MS

TABLE 1

VARIETY DESCRIPTION INFORMATION
25W36

1. KIND: 1
   1 = Common 2 = Durum 3 = Club 4 = Other
2. VERNALIZATION: 2
   1 = Spring 2 = Winter 3 = Other
3. COLEOPTILE ANTHOCYANIN: 1
   1 = Absent 2 = Present
4. JUVENILE PLANT GROWTH: 2
   1 = Prostrate 2 = Semi-erect 3 = Erect
5. PLANT COLOR (boot stage): 2
   1 = Yellow-Green 2 = Green 3 = Blue-Green
6. FLAG LEAF (boot stage): 2
   1 = Erect 2 = Recurved
   FLAG LEAF (boot stage): 2
   1 = Not Twisted 2 = Twisted
7. EAR EMERGENCE: 1 = Number of Days earlier than 2737W
8. ANTHER COLOR: 1
   1 = Yellow 2 = Purple
9. PLANT HEIGHT (from soil to top of head, excluding awns):
   5 cm Taller than 2737W
   0 cm Shorter than
10. STEM:
    A. ANTHOCYANIN: 1
    1 = Absent 2 = Present
    B. WAXY BLOOM: 2
    1 = Absent 2 = Present
    C. HAIRINESS (last internode of rachis): 2
    1 = Absent 2 = Present
    D. INTERNODE: 1 (number: 6)
    1 = Hollow 2 = Semi-solid 3 = Solid
    E. PEDUNCLE 1
    1 = Erect 2 = Recurved 3 = Semi-erect
    F. AURICLE
    Anthocyanin: 2
    1 = Absent 2 = Present
    Hair: 2
    1 = Absent 2 = Present
11. HEAD (at maturity)
    A. DENSITY: 2
    1 = Lax 2 = Middense 3 = Dense
    B. SHAPE: 1
    1 = Tapering 2 = Strap 3 = Clavate 4 = Other
    C. CURVATURE: 3
    1 = Erect 2 = Inclined 3 = Recurved
    D. AWNEDNESS: 2
    1 = Awnless 2 = Apically Awnletted 3 = Awnletted 4 = Awned
12. GLUMES (at Maturity):
    A. COLOR: 3 (white/amber)
    1 = White 2 = Tan 3 = Other
    B. SHOULDER: 3
    1 = Wanting 2 = Oblique 3 = Rounded 4 = Square 5 = Elevated
    6 = Apiculate
    C. SHOULDER WIDTH: 2
    1 = Narrow 2 = Medium 3 = Wide
    D. BEAK: 2
    1 = Obtuse 2 = Acute 3 = Acuminate
    E. BEAK WIDTH: 2
    1 = Narrow 2 = Medium 3 = Wide
    F. GLUME LENGTH: 2
    1 = Short (ca. 7 mm) 2 = Medium (ca. 8 mm) 3 = Long (ca. 9 mm)
    G. GLUME WIDTH: 3
    1 = Narrow (ca. 3 mm) 2 = Medium (ca. 3.5 mm) 3 = Wide (ca. 4 mm)
13. SEED:
    A. SHAPE: 1
    1 = Ovate 2 = Oval 3 = Elliptical
    B. CHEEK: 1
    1 = Rounded 2 = Angular
    C. BRUSH: 2
    1 = Short 2 = Medium 3 = Long
    BRUSH: 1

TABLE 1-continued

VARIETY DESCRIPTION INFORMATION
25W36

1 = Not Collared 2 = Collared
D. CREASE: 1
1 = Width 60% or less of Kernel
2 = Width 80% or less of Kernel
3 = Width Nearly as Wide as Kernel
CREASE: 1
1 = Depth 20% or less of Kernel
2 = Depth 35% or less of Kernel
3 = Depth 50% or less of Kernel
E. COLOR: 1
1 = White 2 = Amber 3 = Red 4 = Other
F. TEXTURE: 2
1 = Hard 2 = Soft
G. PHENOL REACTION: 4
1 = Ivory 2 = Fawn 3 = Light Brown 4 = Dark Brown 5 = Black
H. SEED WEIGHT: 36
g/100 Seed
I. GERM SIZE: 2
1 = Small 2 = Midsize 3 = Large
14. DISEASE: (0 = Not tested 1 = Susceptible 2 = Resistant
    3 = Intermediate 4 = Tolerant)
    SPECIFIC RACE OR STRAIN TESTED
    Stem Rust (*Puccinia graminis* f. sp. *tritici*): 0
    Stripe Rust (*Puccinia striiformis*): 2
    Tan Spot (*Pyrenophora tritici-repentis*): 3
    Halo Spot (*Selenophoma donacis*): 0
    *Septoria nodorum* (Glume Blotch): 3
    *Septoria avenae* (Speckled Leaf Disease): 0
    *Septoria tritici* (Speckled Leaf Blotch): 3
    Scab (*Fusarium* spp.): 3
    Leaf Rust (*Puccinia recondite* f. sp. *tritici*): 3
    Loose Smut (*Ustilago tritici*): 0
    Flag Smut (*Urocystis agropyri*): 0
    Common Bunt (*Tilletia tritici* or *T. laevis*): 0
    Dwarf Bunt (*Tilletia controversa*): 0
    Karnal Bunt (*Tilletia indica*): 0
    Powdery Mildew (*erysiphe graminis* f. sp. *tritici*): 3
    "Snow Molds": 0
    "Black Point" (Kernel Smudge): 0
    Barley Yellow Dwarf Virus (BYDV): 0
    Soilborne Mosaic Virus (SBMV): 1
    Wheat Yellow (Spindle Streak) Mosaic Virus 3
    Wheat Streak Mosaic Virus (WSMV): 0
    Common Root Rot (*Fusarium, Cochliobolus,* and
    *Bipolaris* spp.): 0
    *Rhizoctonia* Root Rot (*Rhizoctonia solani*): 0
    Black Chaff (*Xanthomonas campestris* pv. *translucens*): 0
    Bacterial Leaf Blight (*pseudomonas syringae* pv. *syringae*): 0
15. INSECT: (0 = Not tested 1 = Susceptible 2 = Resistant
    3 = Intermediate 4 = Tolerant)
    Hessian Fly (*Mayetiola destructor*): 1
    Biotype L
    Stem Sawfly (*Cephus* spp.): 0
    Cereal Leaf Beetle (*Oulema melanopa*): 0
    Russian Aphid (*Diuraphis noxia*): 0
    Greenbug (*schizaphis graminum*): 0
    Aphids: 0

For more information on descriptive factors see "Objective Description of Variety Wheat (Triticum supp.)" which is a part of "Application for Plant Variety Protection Certificate" distributed by U.S. Department of Agriculture, Agricultural Marketing Service, Science and Technology, Plant Variety Protection Office, Beltsville Md. 20705. All colors are defined using Munsell Color Charts for Plant Tissues.

FURTHER EMBODIMENTS OF THE INVENTION

Further reproduction of the wheat variety 25W36 can occur by tissue culture and regeneration. Tissue culture of various tissues of wheat and regeneration of plants therefrom is well known and widely published. A review of various wheat tissue culture protocols can be found in "In Vitro Culture of Wheat and Genetic Transformation-Retrospect and Prospect" by Maheshwari et al. (*Critical Reviews in Plant Sciences,* 14(2): pp 149-178, 1995). Thus, another aspect of this invention is to provide cells which upon growth and differentiation produce wheat plants capable of having the physiological and morphological characteristics of wheat variety 25W36.

As used herein, the term plant parts includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes". Over the last fifteen to twenty years several methods for producing transgenic plants have been developed, and the present invention, in particular embodiments, also relates to transformed versions of the wheat variety 25W36.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology,* Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology,* Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

Various genetic elements can be introduced into the plant genome using transformation. These elements include but are not limited to genes; coding sequences; inducible, constitutive, and tissue specific promoters; enhancing sequences; and signal and targeting sequences.

A genetic trait which has been engineered into a particular wheat plant using transformation techniques, could be moved into another line using traditional breeding techniques that are well known in the plant breeding arts. For example, a backcrossing approach could be used to move a transgene from a transformed wheat plant to an elite wheat variety and the resulting progeny would comprise a transgene. As used herein, "crossing" can refer to a simple X by Y cross, or the process of backcrossing, depending on the context. The term "breeding cross" excludes the processes of selfing or sibbing.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a wheat plant. In another preferred embodiment, the biomass of interest is seed. A genetic map can be generated, primarily via conventional RFLP, PCR, and SSR analysis, which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Through the transformation of wheat the expression of genes can be modulated to enhance disease resistance, insect resistance, herbicide resistance, water stress tolerance and agronomic traits as well as grain quality traits. Transformation can also be used to insert DNA sequences which control or help control male-sterility. DNA sequences native to wheat as well as non-native DNA sequences can be transformed into wheat and used to modulate levels of native or non-native proteins. Anti-sense technology, various promoters, targeting sequences, enhancing sequences, and other DNA sequences can be inserted into the wheat genome for the purpose of modulating the expression of proteins. Exemplary genes implicated in this regard include, but are not limited to, those categorized below.

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. *tomato* encodes a protein kinase); Mindrinos et al., Cell 78:1089 (1994) (*Arabidopsis* RSP2 gene for resistance to *Pseudomonas syringae*); McDowell & Woffenden, (2003) Trends Biotechnol. 21(4):178-83 and Toyoda et al., (2002) Transgenic Res. 11(6):567-82. A plant resistant to a disease is one that is more resistant to a pathogen as compared to the wild type plant.

*Fusarium* head blight along with deoxynivalenol both produced by the pathogen *Fusarium graminearum* Schwabe have caused devastating losses in wheat production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavoniods, lactoferricin. During infection with *Fusarium graminearum* deoxynivalenol is produced. There is evidence that production of deoxynivalenol increases the virulence of the disease. Genes with properties for detoxification of deoxynivalenol (Adam and Lemmens, In International Congress on Molecular Plant-Microbe Interactions, 1996; McCormick et al. Appl. Environ. Micro. 65:5252-5256, 1999) have been engineered for use in wheat. A synthetic peptide that competes with deoxynivalenol has been identified (Yuan et al., Appl. Environ. Micro. 65:3279-3286, 1999). Changing the ribosomes of the host so that they have reduced affinity for deoxynivalenol has also been used to reduce the virulence of the *Fusarium graminearum*.

Genes used to help reduce *Fusarium* head blight include but are not limited to Tri101(Fusarium), PDR5 (yeast), tlp-1 (oat), tip-2(oat), leaf tlp-1 (wheat), tlp (rice), tlp-4 (oat), endochitinase, exochitinase, glucanase (Fusarium), permatin (oat), seed hordothionin (barley), alpha-thionin (wheat), acid glucanase (alfalfa), chitinase (barley and rice), class beta II-1,3-glucanase (barley), PR5/tlp (arabidopsis), zeamatin (maize), type 1 RIP (barley), NPR1 (arabidopsis), lactoferrin (mammal), oxalyl-CoA-decarboxylase (bacterium), IAP (baculovirus), ced-9 (*C. elegans*), and glucanase (rice and barley).

(B) A gene conferring resistance to a pest, such as Hessian fly, wheat, stem soft fly, cereal leaf beetle, and/or green bug. For example the H9, H10, and H21 genes.

(C) A gene conferring resistance to disease, including wheat rusts, septoria tritici, septoria nodorum, powdery mildew, helminthosporium diseases, smuts, bunts, fusarium diseases; bacterial diseases, and viral diseases (D) A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(E) An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

(F) An insect-specific peptide which, upon expression, disrupts the physiology of the affected pest. For example, see the disclosures of Regan, *J. Biol. Chem.* 269:9 (1994) (expression cloning yields DNA coding for insect diuretic hormone receptor); Pratt et al., *Biochem. Biophys. Res. Comm.* 163: 1243 (1989) (an allostatin is identified in *Diploptera punctata*); Chattopadhyay et al. (2004) Critical Reviews in Microbiology 30 (1):33-54 2004; Zjawiony (2004) J Nat Prod 67 (2):300-310; Carlini & Grossi-de-Sa (2002) Toxicon, 40 (11): 1515-1539; Ussuf et al. (2001) Curr Sci. 80 (7):847-853; and Vasconcelos & Oliveira (2004) Toxicon 44 (4):385-403. See also U.S. Pat. No. 5,266,317 to Tomalski et al., who disclose genes encoding insect-specific toxins.

(G) An enzyme responsible for an hyperaccumulation of a monterpene, a sesquiterpene, a steroid, hydroxamic acid, a phenylpropanoid derivative or another non-protein molecule with insecticidal activity.

(H) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application No. WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi-4-2 polyubiquitin gene, U.S. application Ser. Nos. 10/389,432, 10/692,367, and U.S. Pat. No. 6,563,020.

(I) A molecule that stimulates signal transduction. For example, see the disclosure by Botella at al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

(J) A hydrophobic moment peptide. See PCT Application No. WO 95/16776 and U.S. Pat. No. 5,580,852 (disclosure of peptide derivatives of Tachyplesin which inhibit fungal plant pathogens) and PCT Application No. WO 95/18855 and U.S. Pat. No. 5,607,914) (teaches synthetic antimicrobial peptides that confer disease resistance).

(K) A membrane permease, a channel former or a channel blocker. For example, see the disclosure by Jaynes et al., *Plant Sci.* 89:43 (1993), of heterologous expression of a cecropin-beta lytic peptide analog to render transgenic tobacco plants resistant to *Pseudomonas solanacearum*.

(L) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(M) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(N) A virus-specific antibody. See, for example, Tavladoraki et al., *Nature* 366:469 (1993), who show that transgenic plants expressing recombinant antibody genes are protected from virus attack.

(O) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology*

10:1436 (1992). The cloning and characterization of a gene which encodes a bean endopolygalacturonase-inhibiting protein is described by Toubart et al., *Plant J.* 2:367 (1992).

(P) A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

(Q) Genes involved in the Systemic Acquired Resistance (SAR) Response and/or the pathogenesis related genes. Briggs, S., Current Biology, 5(2):128-131 (1995), Pieterse & Van Loon (2004) Curr. Opin. Plant Bio. 7(4):456-64 and Somssich (2003) Cell 113(7):815-6.

(R) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. application Ser. No. 09/950,933.

(S) Detoxification genes, such as for fumonisin, beauvericin, moniliformin and zearalenone and their structurally related derivatives. For example, see U.S. Pat. No. 5,792,931

(T) Cystatin and cysteine proteinase inhibitors. See U.S. application Ser. No. 10/947,979.

(U) Defensin genes. See WO 03/000863 and U.S. application Ser. No. 10/178,213.

(V) Genes conferring resistance to nematodes. See WO 03/033651 and Urwin et. al., Planta 204:472-479 (1998), Williamson (1999) Curr Opin Plant Bio. 2(4):327-31.

2. Genes that Confer Resistance to a Herbicide, for Example:

(A) Acetohydroxy acid synthase, which has been found to make plants that express this enzyme resistant to multiple types of herbicides, has been introduced into a variety of plants (see, e.g., Hattori et al. (1995) *Mol Gen Genet* 246: 419). Other genes that confer tolerance to herbicides include: a gene encoding a chimeric protein of rat cytochrome P4507A1 and yeast NADPH-cytochrome P450 oxidoreductase (Shiota et al. (1994) *Plant Physiol Plant Physiol* 106:17), genes for glutathione reductase and superoxide dismutase (Aono et al. (1995) *Plant Cell Physiol* 36:1687, and genes for various phosphotransferases (Datta et al. (1992) *Plant Mol Biol* 20:619).

(B) A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively. See also, U.S. Pat. Nos. 5,605,011; 5,013,659; 5,141, 870; 5,767,361; 5,731,180; 5,304,732; 4,761,373; 5,331,107; 5,928,937; and 5,378,824; and international publication WO 96/33270, which are incorporated herein by reference for this purpose.

(C) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627, 061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491, 288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, PCT International Publication No. WO 01/46227 and 10/427,692 and 10/427,692. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricinacetyl-transferase gene is provided in European Patent No. 0 242 246 and 0 242 236 to Leemans et al. De Greef et al., *Bio/Technology* 7:61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879, 903, which are incorporated herein by reference for this purpose. Exemplary genes conferring resistance to phenoxy proprionic acids and cycloshexones, such as sethoxydim and haloxyfop, are the Acc1-S1, Acc1-S2 and Acct-S3 genes described by Marshall et al., *Theor. Appl. Genet.* 83:435 (1992).

(D) A herbicide that inhibits photosynthesis, such as a triazine (psbA and gs+ genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Genes that Confer or Improve Grain Quality, Such as:

(A) Altered fatty acids, for example, by (1) Down-regulation of stearoyl-ACP desaturase to increase stearic acid content of the plant. See Knultzon et al., *Proc. Natl. Acad. Sci. USA* 89:2624 (1992) and WO 99/64579 (Genes for Desaturases to Alter Lipid Profiles in Corn), (2) Elevating oleic acid via FAD-2 gene modification and/ or decreasing linolenic acid via FAD-3 gene modification (see U.S. Pat. Nos. 6,063,947; 6,323,392; 6,372,965 and WO 93/11245), (3) Altering conjugated linolenic or linoleic acid content, such as in WO 01/12800, (4) Altering LEC1, AGP, Dek1, Superal1, milps, various Ipa genes such as Ipa1, Ipa3, hpt or hggt. For example, see WO 02/42424, WO 98/22604, WO 03/011015, U.S.

Pat. Nos. 6,423,886, 6,197,561, 6,825,397; US2003/0079247, US2003/0204870, WO 02/057439, WO 03/011015 and Rivera-Madrid, R. et. al. Proc. Natl. Acad. Sci. 92:5620-5624 (1995).

(B) Altered phosphorus content, for example, by the
(1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene.
(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., *Maydica* 35:383 (1990) and/or by altering inositol kinase activity as in WO 02/059324, US2003/0009011, WO 03/027243, US2003/0079247, WO 99/05298, U.S. Pat. Nos. 6,197, 561, 6,291,224, 6,391,348; WO 02/059324, US2003/0079247, WO 98/45448, WO 99/55882, WO 01/04147.

(C) Altered carbohydrates effected, for example, by altering a gene for an enzyme that affects the branching pattern of starch or a gene altering thioredoxin (See U.S. Pat. No. 6,531, 648). See Shiroza et al., J. Bacteriol. 170:810 (1988) (nucleotide sequence of *Streptococcus mutans* fructosyltransferase gene), Steinmetz et al., Mol. Gen. Genet. 200:220 (1985) (nucleotide sequence of *Bacillus subtilis* levansucrase gene), Pen et al., Bio/Technology 10:292 (1992) (production of transgenic plants that express *Bacillus licheniformis* alpha-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley alpha-amylase gene), and Fisher et al., Plant Physiol. 102:1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 99/40209 (alteration of amino acid compositions in seeds), WO 99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 98/56935 (plant amino acid biosynthetic enzymes), WO 98/45458 (engineered seed protein having higher percentage of essential amino acids), WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 96/01905 (increased threonine), WO 95/15392 (increased lysine), US2003/0163838, US2003/0150014, US2004/0068767, U.S. Pat. No. 6,803,498, WO 01/79516, and WO 00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage (Maeser et al., 1991; Vicki Chandler, *The Maize Handbook* ch. 118 (Springer-Verlag 1994), the Pin recombinase of *E. coli* (Enomoto et al., 1983), and the R/RS system of the pSRi plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104; WO 00/060089, WO 01/026459, WO 01/035725, WO 01/034726, WO 01/035727, WO 01/036444, WO 01/036597, WO 01/036598, WO 02/015675, WO 02/017430, WO 02/077185, WO 02/079403, WO 03/013227, WO 03/013228, WO 03/014327, WO 04/031349, WO 04/076638, WO 98/09521, and WO 99/38977 describing genes, including CBF genes and transcription factors effective in mitigating the negative effects of freezing, high salinity, and drought on plants, as well as conferring other positive effects on plant phenotype; US2004/0148654 and WO 01/36596 where abscisic acid is altered in plants resulting in improved plant phenotype such as increased yield and/or increased tolerance to abiotic stress; WO 00/006341, WO 04/090143, U.S. application Ser. Nos. 10/817,483 and 09/545,334 where cytokinin expression is modified resulting in plants with increased stress tolerance, such as drought tolerance, and/or increased yield. Also see WO 02/02776, WO 03/052063, JP2002281975, U.S. Pat. No. 6,084,153, WO 01/64898, U.S. Pat. Nos. 6,177,275, and 6,107,547 (enhancement of nitrogen utilization and altered nitrogen responsiveness). For ethylene alteration, see US2004/0128719, US2003/0166197 and WO 00/32761. For plant transcription factors or transcriptional regulators of abiotic stress, see e.g. US2004/0098764 or US2004/0078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. No. 6,794,560, U.S. Pat. No. 6,307,126 (GAI), WO 99/09174 (D8 and Rht), and WO 04/076638 and WO 04/031349 (transcription factors).

7. Genes that Confer Agronomic Enhancements, Nutritional Enhancements, or Industrial Enhancements.

(A) Improved tolerance to water stress from drought or high salt water condition. The HVA1 protein belongs to the group 3 LEA proteins that include other members such as wheat pMA2005 (Curry et al., 1991; Curry and Walker-Simmons, 1993), cotton D-7 (Baker et al., 1988), carrot Dc3 (Seffens et al., 1990), and rape pLEA76 (Harada et al., 1989). These proteins are characterized by 11-mer tandem repeats of amino acid domains which may form a probable amphophilic alpha-helical structure that presents a hydrophilic surface with a hydrophobic stripe (Baker et al., 1988; Dure et al., 1988; Dure, 1993). The barley HVA1 gene and the wheat pMA2005 gene (Curry et al., 1991; Curry and Walker-Simmons, 1993) are highly similar at both the nucleotide level and predicted amino acid level. These two monocot genes are closely related to the cotton D-7 gene (Baker et al., 1988) and carrot Dc3 gene (Seffens et al., 1990) with which they share a similar structural gene organization (Straub et al., 1994). There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried and Walker-Simmons, 1993). Studies on several Indica varieties of rice showed that the levels of group 2 LEA proteins (also known as dehydrins) and group 3 LEA proteins in roots were significantly higher in salt-tolerant varieties compared with sensitive varieties (Moons et al., 1995). The barley HVA1 gene was transformed into wheat. Transformed wheat plants showed increased tolerance to water stress, (Sivamani, E. et al. Plant Science 2000, V. 155 p 1-9 and U.S. Pat. No. 5,981,842.)

(B) Another example of improved water stress tolerance is through increased mannitol levels via the bacterial mannitol-1-phosphate dehydrogenase gene. To produce a plant with a genetic basis for coping with water deficit, Tarczynski et al. (Proc. Natl. Acad. Sci. USA, 89, 2600 (1992); WO 92/19731, published No. 12, 1992; Science, 259, 508 (1993)) introduced the bacterial mannitol-1-phosphate dehydrogenase gene, mtlD, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski et al. compared the growth of transgenic plants to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level. See also U.S. Pat. No. 5,780,709 and international publication WO 92/19731 which are incorporated herein by reference for this purpose.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

Further embodiments of the invention are the treatment of 25W36 with a mutagen and the plant produced by mutagenesis of 25W36. Information about mutagens and mutagenizing seeds or pollen are presented in the *IAEA's Manual on Mutation Breeding* (IAEA, 1977) other information about mutation breeding in wheat can be found in C. F. Konzak, "Mutations and Mutation Breeding" chapter 7B, of *Wheat and Wheat Improvement*, $2^{nd}$ edition, ed. Heyne, 1987.

A further embodiment of the invention is a backcross conversion of wheat variety 25W36. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male steriltiy. Descriptions of some of the cytoplasmic male sterility genes, nuclear male sterility genes, chemical hybridizing agents, male fertility restoration genes, and methods of using the aforementioned are discussed in "Hybrid Wheat" by K. A. Lucken (pp. 444-452 In *Wheat and Wheat Improvement*, ed. Heyne, 1987). Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), Powdery Mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtlD). The trait of interest is transferred from the donor parent to the recurrent parent, in this case, the wheat plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Another embodiment of this invention is a method of developing a backcross conversion 25W36 wheat plant that involves the repeated backcrossing to wheat variety 25W36. The number of backcrosses made may be 2, 3, 4, 5, 6 or greater, and the specific number of backcrosses used will depend upon the genetics of the donor parent and whether molecular markers are utilized in the backcrossing program. See, for example, R. E. Allan, "Wheat" in Principles of Cultivar Development, Fehr, W. R. Ed. (Macmillan Publishing Company, New York, 1987) pages 722-723, incorporated herein by reference. Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, or 99% of the genetic profile of wheat variety 25W36. The percentage of the genetics retained in the backcross conversion may be measured by either pedigree analysis or through the use of genetic techniques such as molecular markers or electrophoresis. In pedigree analysis, on average 50% of the starting germplasm would be passed to the progeny line after one cross to another line, 75% after backcrossing once, 87.5% after backcrossing twice, and so on. Molecular markers could also be used to confirm and/or determine the recurrent parent used. The backcross conversion developed from this method may be similar to 25W36 for the results listed in Table 1. Such similarity may be measured by a side by side phenotypic comparison, with differences and similarities determined at a 5% significance level. Any such comparison should be made in environmental conditions that account for the trait being transferred. For example, herbicide should not be applied in the phenotypic comparison of herbicide resistant backcross conversion of 25W36 to 25W36.

Another embodiment of the invention is an essentially derived variety of 25W36. As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of 25W36 is further defined as one whose production requires the repeated use of variety 25W36 or is predominately derived from variety 25W36. International Convention for the Protection of New Varieties of Plants, as amended on Mar. 19, 1991, Chapter V, Article 14, Section 5(c).

This invention also is directed to methods for using wheat variety 25W36 in plant breeding.

One such embodiment is the method of crossing wheat variety 25W36 with another variety of wheat to form a first generation population of F1 plants. The population of first generation F1 plants produced by this method is also an embodiment of the invention. This first generation population of F1 plants will comprise an essentially complete set of the alleles of wheat variety 25W36. One of ordinary skill in the art can utilize either breeder books or molecular methods to identify a particular F1 plant produced using wheat variety 25W36, and any such individual plant is also encompassed by this invention. These embodiments also cover use of transgenic or backcross conversions of wheat variety 25W36 to produce first generation F1 plants.

A method of developing a 25W36-progeny wheat plant comprising crossing 25W36 with a second wheat plant and performing a breeding method is also an embodiment of the invention. A specific method for producing a line derived from wheat variety 25W36 is as follows. One of ordinary skill in the art would cross wheat variety 25W36 with another variety of wheat, such as an elite variety. The F1 seed derived from this cross would be grown to form a homogeneous population. The F1 seed would contain one set of the alleles from variety 25W36 and one set of the alleles from the other wheat variety. The F1 genome would be made-up of 50% variety 25W36 and 50% of the other elite variety. The F1 seed would be grown and allowed to self, thereby forming F2 seed. On average the F2 seed would have derived 50% of its alleles from variety 25W36 and 50% from the other wheat variety, but various individual plants from the population would have a much greater percentage of their alleles derived from 25W36 (Wang J. and R. Bernardo, 2000, Crop Sci. 40:659-665 and Bernardo, R. and A. L. Kahler, 2001, Theor. Appl. Genet. 102:986-992). The F2 seed would be grown and selection of plants would be made based on visual observation and/or measurement of traits. The 25W36-derived progeny that exhibit one or more of the desired 25W36-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable 25W36-derived traits. The process of growing and selection would be repeated any number of times until a homozygous 25W36-derived wheat plant is obtained. The homozygous 25W36-derived wheat plant would contain desirable traits derived from wheat variety 25W36, some of which may not have been expressed by the other original wheat variety to which wheat variety 25W36 was crossed and some of which may have been expressed by both wheat varieties but now would be at a level equal to or greater than the level expressed in wheat variety 25W36. The homozygous 25W36-derived wheat plants would have, on average, 50% of their genes derived from wheat variety 25W36, but various individual plants from the population would have a much greater percentage of their alleles derived from 25W36. The breeding process, of crossing, selfing, and selection may be repeated to produce another population of 25W36-derived wheat plants with, on average, 25% of their genes derived from wheat variety 25W36, but various individual plants from the population would have a much greater percentage of their alleles derived from 25W36. Another embodiment of the invention is a homozygous 25W36-derived wheat plant that has received 25W36-derived traits.

The modified pedigree selection method of breeding was used to derive this line from elite germplasm. The first cross was made in 1995 and breeding continued until August 2007. 25W36 represents a significant advancement in elite germplasm adapted to the United States.

The previous example can be modified in numerous ways, for instance selection may or may not occur at every selfing generation, selection may occur before or after the actual self-pollination process occurs, or individual selections may be made by harvesting individual spikes, plants, rows or plots at any point during the breeding process described. In addition, double haploid breeding methods may be used at any step in the process. The population of plants produced at each and any generation of selfing is also an embodiment of the invention, and each such population would consist of plants containing approximately 50% of its genes from wheat variety 25W36, 25% of its genes from wheat variety 25W36 in the second cycle of crossing, selfing, and selection, 12.5% of its genes from wheat variety 25W36 in the third cycle of crossing, selfing, and selection, and so on.

Another embodiment of this invention is the method of obtaining a homozygous 25W36-derived wheat plant by crossing wheat variety 25W36 with another variety of wheat and applying double haploid methods to the F1 seed or F1 plant or to any generation of 25W36-derived wheat obtained by the selfing of this cross.

Still further, this invention also is directed to methods for producing 25W36-derived wheat plants by crossing wheat variety 25W36 with a wheat plant and growing the progeny seed, and repeating the crossing or selfing along with the growing steps with the 25W36-derived wheat plant from 1 to 2 times, 1 to 3 times, 1 to 4 times, or 1 to 5 times. Thus, any and all methods using wheat variety 25W36 in breeding are part of this invention, including selfing, pedigree breeding, backcrossing, hybrid production and crosses to populations. Unique starch profiles, molecular marker profiles and/or breeding records can be used by those of ordinary skill in the art to identify the progeny lines or populations derived from these breeding methods.

Performance Examples of 25W36

In the examples that follow, the traits and characteristics of wheat variety 25W36 are given in paired comparisons with another variety during the same growing conditions and the same year. The data collected on each wheat variety is presented for key characteristics and traits.

The results in Table 2 compare variety 25W36 to varieties 2737W, 25W33 and 25W41 for various agronomic traits. The results show that variety 25W36 had significantly higher winter hardiness compared to 25W33 and 25W41. Wheat variety 25W36 also had significantly higher resistance to leaf blight compared to, 25W33 and 25W41.

The results in Table 3 show values for the grain quality of variety 25W36 and comparison varieties 2737W, 25W33 and 25W41. Quality data were collected from 2002-2006 at USDA-ARS Soft Wheat Quality Lab in Wooster, Ohio.

TABLE 2

Paired comparisons of 25W36 during the period 2002-2006.

| Variety | Grain Yield bu/ac | Test Weight lb/bu | Plant Height cm | Heading Date After Jan 1 | Winter hardiness 1-9@ | Straw Lodging 1-9@ | Leaf Rust 1-9@ |
|---|---|---|---|---|---|---|---|
| 25W36 | 102.2 | 57.5 | 96.5 | 146.4 | 7.8 | 7.0 | 6.0 |
| 2737W | 94.1 | 55.7 | 91.4 | 147.0 | 7.8 | 7.3 | 6.0 |
| Locations | 28 | 27 | 11 | 11 | 2 | 3 | 1 |
| Reps. | 52 | 51 | 20 | 21 | 4 | 6 | 2 |
| Prob. | 0.00 | 0.00 | 0.01 | 0.26 | 1.00 | 0.80 | |
| 25W36 | 98.8 | 57.2 | 94.0 | 148.4 | 7.8 | 7.0 | 6.0 |
| 25W33 | 94.9 | 56.5 | 86.4 | 148.7 | 5.8 | 6.8 | 6.9 |
| Locations | 42 | 41 | 14 | 15 | 2 | 3 | 2 |
| Reps. | 90 | 90 | 32 | 37 | 4 | 6 | 5 |
| Prob. | 0.00 | 0.06 | 0.00 | 0.01 | 1.00 | 0.90 | 0.36 |
| 25W36 | 100.4 | 57.1 | 94.0 | 148.5 | 7.8 | 6.0 | 6.0 |
| 25W41 | 97.5 | 57.9 | 88.9 | 148.0 | 5.8 | 6.5 | 8.0 |
| Locations | 47 | 43 | 16 | 17 | 2 | 4 | 2 |
| Reps. | 112 | 99 | 40 | 45 | 4 | 10 | 5 |
| Prob. | 0.00 | 0.03 | 0.00 | 0.13 | 0.30 | 0.39 | 1.00 |

| Variety | Leaf Blight 1-9@ | Powdery Mildew 1-9@ | Scab 1-9@ | Stripe Rust 1-9@ | SBMV 1-9@ | SSMV 1-9@ |
|---|---|---|---|---|---|---|
| 25W36 | 6.2 | 6.3 | 5.2 | 9.0 | 4.5 | 7.0 |
| 2737W | 4.5 | 5.5 | 4.0 | 2.0 | 7.0 | 6.5 |
| Locations | 3 | 2 | 3 | 1 | 4 | 1 |
| Reps. | 6 | 4 | 5 | 1 | 8 | 2 |
| Prob. | 0.27 | 0.20 | 0.12 | | 0.03 | |
| 25W36 | 6.2 | 6.6 | 5.2 | 9.0 | 4.5 | 7.0 |
| 25W33 | 3.7 | 7.3 | 4.8 | 9.0 | 3.4 | 6.0 |
| Locations | 3 | 3 | 3 | 1 | 4 | 1 |
| Reps. | 6 | 8 | 5 | 1 | 8 | 2 |
| Prob. | 0.35 | 0.18 | 0.74 | | 0.14 | |
| 25W36 | 6.2 | 6.6 | 5.2 | 9.0 | 4.5 | 7.0 |
| 25W41 | 5.2 | 5.8 | 6.7 | 4.0 | 7.4 | 6.5 |
| Locations | 3 | 3 | 3 | 1 | 4 | 1 |
| Reps. | 6 | 8 | 5 | 1 | 8 | 2 |
| Prob. | 0.32 | 0.33 | 0.10 | | 0.01 | |

TABLE 3

Average soft wheat quality data, 2002-2006.

| Variety | Flour Yield % | Break Flour Yield % | Flour Protein % | Cookie Diameter cm | Lactic Acid SRC % | Sucrose SRC % |
|---|---|---|---|---|---|---|
| 25W36 | 72.2 | 42.8 | 7.7 | 18.6 | 86.4 | 80.7 |
| Years(reps) | 4(7) | 4(7) | 3(6) | 3(3) | 4(7) | 3(3) |
| 2737W | 72.9 | 42.6 | 8.2 | 18.8 | 93.3 | 83.5 |
| Years(reps) | 4(7) | 4(7) | 3(6) | 3(3) | 4(7) | 3(3) |
| 25W33 | 72.9 | 44.3 | 7.7 | 18.5 | 112.9 | 83.1 |
| Years(reps) | 4(8) | 4(8) | 3(6) | 4(4) | 4(8) | 3(3) |
| 25W41 | 71.4 | 44.0 | 7.9 | 18.9 | 95.3 | 85.2 |
| Years(reps) | 4(8) | 4(8) | 3(6) | 4(4) | 4(8) | 3(3) |

Lactic Acid SRC = Lactic Acid Solvent Retention Capacity
Sucrose SRC = Sucrose solution Retention Capacity Deposit Applicant(s) made a deposit of at least 2500 seeds of Wheat Variety 25W36 with the American Type Culture Collection (ATCC), Manassas, Va. 20110 USA, ATCC Deposit No. PTA-10933. The seeds deposited with the ATCC on May 10, 2010 were taken from the deposit maintained by Pioneer Hi-Bred International, Inc., 7100 NW 62nd Avenue, Johnston, Iowa 50131-1000 since prior to the filing date of this application. Access to this deposit will be available during the pendency of the application to the Commissioner of Patents and Trademarks and persons determined by the Commissioner to be entitled thereto upon request. Upon issue of claims, the Applicant(s) will make available to the public, pursuant to 37 CFR 1.808, a deposit of at least 2500 seeds of variety 25W36 with the American type Culture Collection (ATCC), 10801 University Boulevard, Manassas, Va. 20110-2209. This deposit of the Wheat Variety 25W36 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have or will satisfy all the requirements of 37 C.F.R. §§1.801-1.809, including providing an indication of the viability of the sample. Applicants have no authority to waive any restrictions imposed by law on the transfer of biological material or its transportation in commerce. Applicants do not waive any infringement of their rights granted under this patent or under the Plant Variety Protection Act (7 USC 2321 et seq.). U.S. Plant Variety Protection of Wheat Variety 25W36 has been applied for under PVP Application No. 200500151. Unauthorized seed multiplication prohibited. U.S. Protected Variety.

The foregoing invention has been described in detail by way of illustration and example for purposes of clarity and understanding. However, it will be obvious that certain changes and modifications such as single locus modifications and mutations, somoclonal variants, variant individuals selected from large populations of the plants of the instant variety and the like may be practiced within the scope of the invention.

All publications, patents and patent applications mentioned in the specification are indicative of the level of those skilled in the art to which this invention pertains. All such publications, patents and patent applications are incorporated by reference herein for the purpose cited to the same extent as if each was specifically and individually restated herein.

What is claimed is:

1. A seed of wheat variety designated 25W36, representative seed of said variety having been deposited under ATCC Accession No. PTA-10933.

2. A wheat plant, or part thereof, produced by growing the seed of claim 1.

3. A tissue culture of regenerable cells produced from the plant of claim 2.

4. A protoplast produced from the tissue culture of claim 3.

5. The tissue culture of claim 2, wherein cells of the tissue culture are produced from a tissue selected from the group consisting of kernel, head, stem, leaves, root, root tip, pollen, ovule, embryo and flower.

6. A wheat plant regenerated from the tissue culture of claim 3, said plant having all the morphological and physiological characteristics of wheat variety 25W36, representative seed of said wheat variety deposited under ATCC Accession No. PTA-10933.

7. A method for producing an F1 wheat seed, comprising crossing the plant of claim 2 with a different wheat plant and harvesting the resulting F1 wheat seed.

8. A method of producing a male sterile wheat plant comprising transforming the wheat plant of claim 2 with a nucleic acid molecule that confers male sterility.

9. A male sterile wheat plant produced by the method of claim 8.

10. A method of producing an herbicide resistant wheat plant comprising transforming the wheat plant of claim 2 with a transgene that confers herbicide resistance.

11. An herbicide resistant wheat plant produced by the method of claim 10.

12. The wheat plant of claim 11, wherein the transgene confers resistance to an herbicide selected from the group consisting of: imidazolinone, sulfonylurea, glyphosate, glufosinate, L-phosphinothricin, triazine and benzonitrile.

13. A method of producing an insect resistant wheat plant comprising transforming the wheat plant of claim 2 with a transgene that confers insect resistance.

14. An insect resistant wheat plant produced by the method of claim 13.

15. The wheat plant of claim 14, wherein the transgene encodes a *Bacillus thuringiensis* endotoxin.

16. A method of producing a disease resistant wheat plant comprising transforming the wheat plant of claim 2 with a transgene that confers disease resistance.

17. A disease resistant wheat plant produced by the method of claim 16.

18. The wheat plant of claim 17, wherein the transgene confers resistance to *Fusarium graminearum* through the detoxification of deoxynivalenol.

19. A method of producing a wheat plant with decreased phytate content comprising transforming the wheat plant of claim 2 with a transgene encoding phytase.

20. A wheat plant with decreased phytate content produced by the method of claim 19.

21. A method of producing a wheat plant with modified fatty acid metabolism, modified protein metabolism or modified carbohydrate metabolism comprising transforming the wheat plant of claim 2 with a transgene encoding a polypeptide selected from the group consisting of modified glutenins, gliadins, stearyl-ACP-desaturase, fructosyltransferase, levasucrase, alpha-amylase, invertase and starch branching enzyme.

22. A wheat plant with modified fatty acid, modified protein metabolism or modified carbohydrate metabolism produced by the method of claim 21.

23. The wheat plant of claim 22 wherein the transgene confers a trait selected from the group consisting of waxy starch and increased amylose starch.

24. A wheat plant, or part thereof, having all the physiological and morphological characteristics of the variety 25W36, representative seed of such line having been deposited under ATCC Accession No. PTA-1093.

25. A method of producing a wheat plant with increased tolerance to water stress comprising transforming the wheat plant of claim 2 with a transgene encoding mannitol-1-phosphate dehydrogenase or late embryogenesis abundant (LEA) proteins.

26. A wheat plant with increased tolerance to water stress produced by the method of claim 25.

27. A method of introducing a desired trait into wheat variety 25W36 comprising:
   (a) crossing 25W36 plants grown from 25W36 seed, representative seed of which has been deposited under ATCC Accession No. PTA-10933, with plants of another wheat line that comprise a desired trait to produce F1 progeny plants, wherein the desired trait is selected from the group consisting of male sterility, herbicide resistance, insect resistance, disease resistance and waxy starch;
   (b) selecting F1 progeny plants that have the desired trait to produce selected F1 progeny plants;
   (c) crossing the selected progeny plants with the 25W36 plants to produce backcross progeny plants;
   (d) selecting for backcross progeny plants that have the desired trait and physiological and morphological characteristics of wheat variety 25W36 listed in Table 1 to produce selected backcross progeny plants; and
   (e) repeating steps (c) and (d) three or more times in succession to produce selected fourth or higher backcross progeny plants that comprise the desired trait and all of the physiological and morphological characteristics of wheat variety 25W36 listed in Table 1 as determined at the 5% significance level when grown in the same environmental conditions.

28. A plant produced by the method of claim 27, wherein the plant has the desired trait and all of the physiological and morphological characteristics of wheat variety 25W36 listed in Table 1 as determined at the 5% significance level when grown in the same environmental conditions.

29. The plant, or part thereof, of claim 28 wherein the desired trait is herbicide resistance and the resistance is conferred to a herbicide selected from the group consisting of: imidazolinone, sulfonylurea, glyphosate, glufosinate, L-phosphinothricin, triazine and benzonitrile.

30. The plant, or part thereof, of claim 28 wherein the desired trait is insect resistance and the insect resistance is conferred by a transgene encoding a *Bacillus thuringiensis* endotoxin.

31. The plant, or part thereof, of claim 28 wherein the desired trait is disease resistance to *fusarium graminearum* and the disease resistance is conferred through the detoxification of deoxynivalenol.

32. The plant, or part thereof, of claim 28 wherein the desired trait is male sterility and the trait is conferred by a cytoplasmic nucleic acid molecule that confers male sterility.

33. A method of modifying fatty acid metabolism, phytic acid metabolism, carbohydrate metabolism, waxy starch content, gluten content, or water stress tolerance in wheat variety 25W36 comprising:
   (a) crossing 25W36 plants grown from 25W36 seed, representative seed of which has been deposited under ATCC Accession No. PTA-10933, with plants of another wheat variety that comprises a nucleic acid molecule encoding a polypeptide selected from the group consisting of phytase, stearyl-ACP desaturase, fructosyltransferase, levansucrase, alpha-amylase, invertase, starch branching enzyme, glutenin, gliadin, mannitol-1-phosphate dehydrogenase and a late embryogenesis abundant (LEA) protein;
   (b) selecting F1 progeny plants that have said nucleic acid molecule to produce selected F1 progeny plants;
   (c) crossing the selected progeny plants with the 25W36 plants to produce backcross progeny plants;
   (d) selecting for backcross progeny plants that have said nucleic acid molecule and physiological and morphological characteristics of wheat variety 25W36 listed in Table 1 to produce selected backcross progeny plants; and
   (e) repeating steps (c) and (d) three or more times in succession to produce selected fourth or higher backcross progeny plants that comprise said nucleic acid molecule and have all of the physiological and morphological characteristics of wheat variety 25W36 listed in Table 1 as determined at the 5% significance level when grown in the same environmental conditions.

34. A plant produced by the method of claim 33, wherein the plant comprises the nucleic acid molecule and has all of the physiological and morphological characteristics of wheat variety 25W36 listed in Table 1 as determined at the 5% significance level when grown in the same environmental conditions.

\* \* \* \* \*

UNITED STATES PATENT AND TRADEMARK OFFICE
CERTIFICATE OF CORRECTION

| | |
|---|---|
| PATENT NO. | : 8,314,315 B1 |
| APPLICATION NO. | : 12/758269 |
| DATED | : November 20, 2012 |
| INVENTOR(S) | : Lively et al. |

It is certified that error appears in the above-identified patent and that said Letters Patent is hereby corrected as shown below:

In the Specifications

Column 11, line 16, delete "tip-2(oat)" and insert -- tlp-2 (oat) --.

Column 12, line 24, after "Botella" delete "at" and insert -- et --.

Column 13, line 37, delete the second occurrence of "Plant Physiol".

Column 14, line 30, delete "Acct-S3" and insert -- Accl-S3 --.

Column 16, line 53, after "phage" insert -- Mu --.

Column 16, line 56, delete "pSRi" and insert -- pSR1 --.

In the Claims

Column 25, line 2, delete "PTA-1093" and insert -- PTA-10933 --.

Signed and Sealed this
Twenty-eighth Day of May, 2013

Teresa Stanek Rea
*Acting Director of the United States Patent and Trademark Office*